United States Patent
Schastak et al.

(10) Patent No.: US 6,410,568 B1
(45) Date of Patent: Jun. 25, 2002

(54) PORPHYRINS AND THEIR USE AS PHOTOSENSITIZER

(75) Inventors: Stanislaw Schastak, Zschortau (DE); Alexander Shulga, Minsk (BY); Frieder Berr; Peter Wiedemann, both of Leipzig (DE)

(73) Assignee: Astrid Schastak, Zschortau (DE)

( * ) Notice: Subject to any disclaimer, the term of this patent is extended or adjusted under 35 U.S.C. 154(b) by 0 days.

(21) Appl. No.: 09/647,239
(22) PCT Filed: Mar. 31, 1999
(86) PCT No.: PCT/EP99/02228
§ 371 (c)(1), (2), (4) Date: Dec. 15, 2000
(87) PCT Pub. No.: WO99/50269
PCT Pub. Date: Oct. 7, 1999

(30) Foreign Application Priority Data

Mar. 31, 1998 (DE) .......................... 198 14 405

(51) Int. Cl.[7] .................... C07D 487/22; A61K 31/409
(52) U.S. Cl. ........................ 514/333; 540/145; 514/410
(58) Field of Search ............... 540/145; 514/410, 514/333

(56) References Cited

FOREIGN PATENT DOCUMENTS

| EP | 0337601 | 10/1989 |
|---|---|---|
| WO | WO9613504 | 5/1996 |
| WO | 9720846 | 6/1997 |
| WO | 9732885 | 9/1997 |
| WO | WO-97/32885 | * 10/1997 |

OTHER PUBLICATIONS

Chernook et al Chem. Phys. Lett. 254 (1996) 229–241.*

* cited by examiner

Primary Examiner—Richard L. Raymond
Assistant Examiner—Kahsay Habte
(74) Attorney, Agent, or Firm—Crowell & Moring LLP

(57) ABSTRACT

The invention relates to new compounds of the general formula:

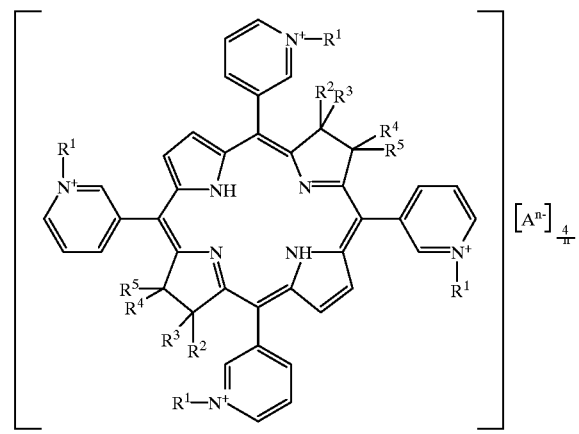

in which:

$R^1$ is $C_1$ to $C_6$ alkyl or aryl, $R^2$ to $R^5$ independently of each other are H, OH, $C_1$ to $C_6$ alkyl, $C_1$ to $C_6$ alkylene or $OR^6$, $R^6$ being $C_1$ to $C_6$ alkyl or aryl, $A^{n-}$ is an anion and n is 1 or 2.

The compounds can be used as photosensitizers for example in medicine, agriculture and industry.

10 Claims, No Drawings

PORPHYRINS AND THEIR USE AS PHOTOSENSITIZER

Photosensitizers are chemical light-sensitive compounds which undergo a photochemical reaction after the absorption of the light quantum. In the biological environment, they are accumulated by both malignant and some pre-malignant cells as a result of the metabolic processes in a higher concentration and also for a longer period than in healthy cells. The photosensitizers are activated by monochromatic laser light of appropriate wavelength and sufficient intensity. The photosensitizer is first excited by light absorption in a relatively short-lived singlet state which then changes into a more stable triplet state. This excited state can be subject to two different reactions.

It can react directly with a substrate and form radicals which form peroxides, hydroxyl radicals, superoxide anion radicals and other products after reaction with the oxygen (type I reaction), or else transfer its energy to oxygen in its basic state and lead to the formation of singlet oxygen $^1O_2$ (type II reaction). For most photosensitizers, an effect via a type II reaction is described. The singlet oxygen is highly reactive and can readily react oxidatively with biomolecules by lifting the ban on spinning (Henderson, B. W. and Dougherty, T. J., How does photodynamic therapy work?, Photochem. Photobiol., 1992, 55, 145–157).

Specific sites or types of cell destruction by PDT are not as yet precisely known. Depending on the type of photosensitizer in question and its charge, this accumulates in particular on cell membranes, in mitochrondria or lysosomes. Damage occurs to membranes through photooxidation of unsaturated fatty acids, lipid-peroxidation and protein-crosslinking (Gomer C. J., Rucker N., Ferrario A., Wong S., Properties and applications of photodynamic therapy, Radiat. Res., 1989, 120, 1–18).

The inhibition of certain membrane-positioned enzymes (Modica-Napoloitano J. S., Joxal J. L., Ara G., Oseroff A. R., Aprille J. R. Mitochrondial toxicity of cationic photosensitizers for phototherapy. Cancer Res., 1990, 50, 7876–7881), a change in the intracellular $Ca^{2+}$-ion concentrations (Hubmer A., Hermann A., Überriegler K., Krammer B., Role of calcium in photodynamically induced cell damage of human fibroblasts, Photochem. Photobiol., 1996, 64, 211–215) and the induction of apoptosis (Luo Y., Chang C. K., Kessel D., Rapid initiation of apoptosis by photodynamic therapy, Photochem. Photobiol., 1996, 63, 528–534) are also discussed.

In medicine, this procedure is called photodynamic therapy (PDT) and is one of the most promising methods of treatment in oncology. PDT is used as the method of choice whenever the patients are either too old or too weak to cope with chemotherapeutic, surgical or radiological operations or when these have already failed. PDT can also be used together with and in addition to other tumor therapies and repeatedly on a patient, the effect being further increased by the synergy effects. The radiation periods are a few minutes, making it necessary to use cw lasers and waveguides for light transport.

Although PDT was already suggested as a method of therapy in 1990 by Raab (Raab O., Über die Wirkung fluoreszierender Stoffe auf Infusoria [The effect of fluorescent substances on infusoria], Z. Biol., 1900, 39, 524–526), significant advances were first achieved only in the 60s, when it was shown that hematoporphyrin derivatives (HPD) can be selectively accumulated in tumor tissue (Lipson R., Baldes E., Olson A., The use of a derivative of hematoporphyrin in tumor detection, J. Natn. Cancer Inst., 1961, 267, 1–8). Extensive tests have since been carried out with HPD (Kessel D. (ed.), Photodynamic Therapy of Neoplastic Disease, Vols. I and II. CRC Press, Boston 1990; Moan J., Porphyrin photosensitization and phototherapy, Photochem. Photobiol., 1986, 43, 681–690; Pass H. I., Photodynamic therapy in oncology: Mechanisms and clinical use, J. Natl. Cancer Inst., 1993, 85, 443–456). Treatment with Photofrin® is currently clinically approved in some countries for some indications.

On the basis of the promising clinical results obtained with Photofrin®, and because of various disadvantages of this substance (low absorption in the range from 700 to 900 nm, i.e. in a range in which the self-absorption of the tissue is minimal, chemical heterogeneity, high and enduring phototoxicity in daylight, inter alia), so-called photosensitizers of the second and third generations are increasingly being synthesized and tested. This group comprises numerous substance classes such as e.g. anthraquinones, anthrapyrazoles, perylene quinones, xanthenes, cyanines, acridines, phenoxazines and phenothiazines (Diwu Z. J., Lown J. W. Phototherapeutic potential of alternative photosensitizers to porphyrins, Pharmac. Ther., 1994, 63, 1–35). The photosensitizers of the third generation are selected according to the following criteria (Gomer C. J., Rucker N., Ferrario A., Wong S. Properties and applications of photodynamic therapy, Radiat. Res., 1989, 120, 1–18):

- chemical purity
- water solubility
- minimal dark toxicity
- significant absorption at wavelengths above 700 nm
- high yields of singlet oxygen
- predominant localisation in pathological tissue (e.g. tumor)
- rapid secretion from normal tissue.

Currently, very intensive research is being carried out on the synthesis of bacteriochlorin derivatives. This is intended to very largely satisfy the above-listed selection criteria (Dougherty T. J. et al. WO 90/12573; Skalkos D. et al. WO 94/00118; Pandey R. K. et al. WO 95/32206; Dolphin D. et al. WO 96/13504; Pandey R. K. et al. WO 97/32885). Some of the newly synthesized bacteriochlorins have a negligible dark toxicity and a high tumor selectivity, are partially water soluble and have marked absorption bands in the range from 700 nm to 810 nm in the so-called "phototherapeutic window". Thus they enable a treatment of tissue layers which lie deeper than 1 cm (Pandey R., Kozyrev A., Potter W. R., Henderson B. W., Bellnier T. J., Dougherty T. J., Long wavelength photosensitizers for photodynamic therapy, Photochem. Photobiol., 1996, 63, Abstracts of the 24th Annual Meeting of the American Soc. for Photobiology, TPM-E6).

Disadvantages of the known bacteriochlorin derivatives are:

- a complicated and expensive synthesis process which usually necessitates a purification of the starting product,
- their poor water solubility which, in the case of a systemic application, results in a dissolution in organic solvents and means an additional chemical burden on the organism,
- their negative or neutral overall charge which rakes absorption by the cells difficult, as they are normally negatively charged,
- chemical instability of the product.

The object of the present invention is to avoid the disadvantages named and to provide photosensitizers, the chemical and physical properties of which allow a technically and economically meaningful use.

This object is achieved by new porphyrins of the following general formula:

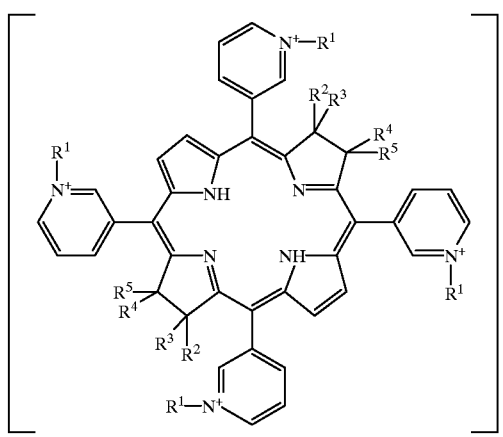

in which:

$R^1$ is $C_1$ to $C_6$ alkyl or aryl, $R^2$ to $R^5$ independently of each other are H, OH, $C_1$ to $C_6$ alkyl, $C_1$ to $C_6$ alkylene or $OR^6$, $R^6$ standing for $C_1$ to $C_6$ alkyl or aryl, $A^{n-}$ is an anion and n is 1 or 2.

The mono- or divalent anion is preferably selected from the group consisting of Cl⁻, Br⁻, I⁻,

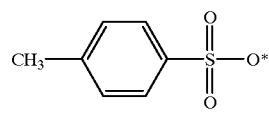

$SO_4^{2-}$.

In a particularly preferred version $R^1$ stands for a $C_1$ to $C_6$ alkyl group, i.e. methyl, ethyl, propyl, butyl, pentyl, hexyl, in particular methyl, the radicals $R^2$ to $R^5$ for H and the anion $A^{n-}$ for

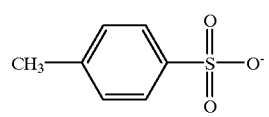

TH new porphyrins can be prepared easily. Porphyrins of the following general structural formula serve as starting products:

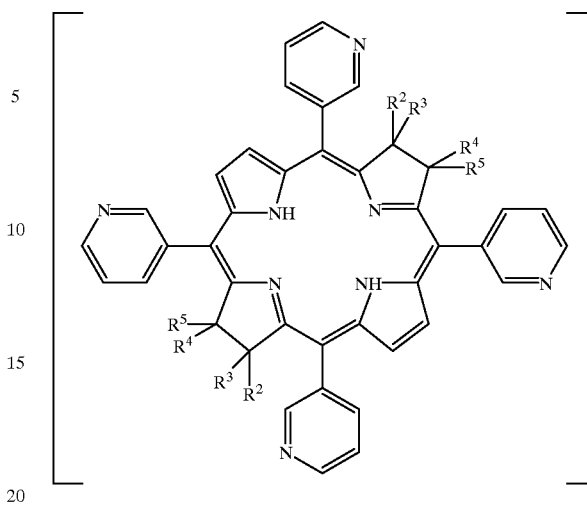

in which $R^2$ to $R^5$ have the above meaning. These products are commercially available or can be easily synthesized from the compound customary in the trade, in which $R^2$ to $R^5$ stand for H.

The starting compounds are reacted with a compound of the general formula $R^1A$ in which $R^1$ and A have the above meaning.

In a preferred version of the process, methyltosylate,

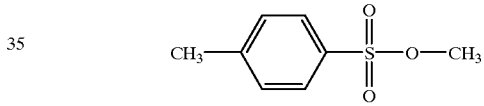

is used as compound $R^1A$.

The new compounds according to the invention belong to the class of tetrakis-pyridyl-porphyrin derivatives and are preferably used as photosensitizers in medicine, agriculture and industry in photodynamic processes. Essential here is the use of the pyridyl derivative of porphins as active photochemical substance. Particularly advantageous is the high water solubility and chemical stability of the new compounds.

Furthermore, the new compounds can be modified by means of metal complexes. In this context there results the possibilities of transporting selected metals (e.g. rare earths etc.) into tumor cells with the aim of accumulating them there. In this way, new absorption lines can be produced in the near-infrared range, which are of interest both for diagnosis and for therapy. When using lanthanides, it is also possible to excite the thus-form sensitizer complex by means of x-ray radiation. Subsequently, this excitement energy is transmitted to the molecular oxygen by means of radiationless or radiant energy transfer processes so that the singlet oxygen is formed as a reactive species.

The new compounds according to the invention are also suitable for the treatment of black melanomas.

Special embodiments of the invention are shown in the following.

PREPARATION EXAMPLE

Synthesis of 5,10,15,20-tetrakis-(1-alkyl-3-pyridyl)-21H, 23H-7,8,17,18-tetrahydroporphyrin-tetra-p-toluene sulphonate 150 mg of tetrakis-(3-pyridyl)-21H,23H-7,8,17,18-tetrahydroporphyrin are dissolved in 15 ml of nitromethane. 350 mg of methyltosilate are then added and the whole is then boiled for 2 hours under a nitrogen atmosphere.

After 2 hours, 120 mg methyltosilate are added and the boiling is continued for 3 hours. After the reaction has ended, the solution is concentrated and left to stand for 12 hours at room temperature. The crystalline sediment is filtered and washed with a benzene-nitromethane solution (1:1).

The yield is 238 mg (100%) 5,10,15,20-tetrakis-(1-alkyl-pyridyl)-21H, 23H-7,8,17,18-tetrahydroporphyrin-tetra-p-toluene sulphonate (THPTPS). This is 72% of the mass of the starting substances.

Chemical formula: $C_{72}H_{70}N_8O_{12}S_4$.

Molecular weight: MW=1367.66.

APPLICATION EXAMPLE

The moment of maximum accumulation of the sensitizer in the cells as a function of the incubation time is determined using a FluoroMax-2 fluorescence spectrometer (Jobbin YVON-Spex Instruments S.A. Inc.). The cells of the choroid melanoma (Schastak S. I., Enzmann V., Jüngel A., Zhavrid E. A., Voropai E. S., Alexandrova E. N., Samtsov M. P., Uugovssky A. P. and P. Wiedemann, Erste Ergebnisse zur PDT des Aderhautmelanoms ex vivo mittels neuer im NIR-Bereich absorbierenden Photosensitizer [First results for the PDT of the choroid melanoma ex vivo by means of new photosensitizers absorbing in the field of NIR range], Lasermedizin 1997, 13: 50–54) as well as the cells of a highly-differentiated gallbladder carcinoma cell line (Wittier) (Purdum, P. P., Cultured human gallbladder epithelia, A carcinoma-derived model, Lab. Invest., 1993, 68: 345–353) and a bile duct adenocarcinoma cell line (Charies), undifferentiated to a high degree (established by Prof. P. Hylemon, Virginia Commonwealth Univ., Richmond, Va., 1996) with a cell count of $1.2 \times 10^6$ cell/ml are incubated in the dark for 1, 6, 12 and 24 hours with the THPTPS sensitizer in a concentration of 0.4 mg/ml or 0.2 mg/ml ($LD_{10}$) Subsequently, they are washed three times in PBS, cleaved off using trypsin, decomposed with ultrasound and centrifuged at 5,000 rpm for 20 minutes. The amount of photosensitizer in the supernatant corresponds exactly to the amount accumulated in the cells. By measuring the intensity in maximum of the emission bands of the THPTPS (($ë_0$=775 nm) after different incubation times, the dependency of the fluorescence intensity on the incubation time, which indicates the moment of maximum absorption of the sensitizers into the cells, is obtained.

To examine the photodynamic effect in vitro, the above-mentioned cell lines were cultivated in a cell count of $2 \times 10^5$ C/ml in DMEM+10% FKS and incubated with the photosensitizer THPTPS in a concentration of 0.2, 0.4, 0.8 mg/ml (Wittier) or 0.4, 0.8, 1.6 mg/ml for 12 hours. Subsequently, they were irradiated with the light of a Ti:Sa leaser with a wavelength of 771 nm and a dose of 15 $J/cm^2$. The evaluation of the irradiation results by means of MTT test (3-[4,5-dimethylthiazol-2-yl]-2,5-diphenyltetrazolium bromide) showed that in the case of the highly-differentiated gallbladder carcinoma cell line approx. 88%, and in the case of the bile duct adenocarcinoma cell line undifferentiated to a high degree, approx. 84%, or the cells are dead. Approximately 88% of the choroid melanoma cells were able to be killed by the irradiation.

What is claimed is:

1. A compound of the general formula:

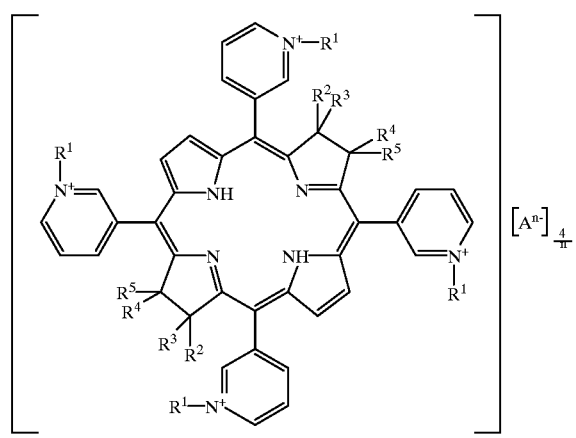

in which:

$R^1$ is $C_1$ to $C_6$ alkyl or aryl, $R^2$ to $R^5$ independently of each other are H, OH, $C_1$ to $C_6$ alkyl, $C_1$ to $C_6$ alkylene or $OR^6$, $R^6$ being $C_1$ to $C_6$ alkyl or aryl, $A^{n-}$ is an anion and n is 1 or 2.

2. A compound according to claim 1, wherein $R^1$ is methyl, ethyl, propyl, butyl, pentyl or hexyl.

3. A compound according to claim 1 or 2 wherein $R^2$ to $R^5$ are each H.

4. A compound according to claim 1 or 2, wherein $A^{n-}$ is selected from $Cl^-$, $Br^-$, $I^-$,

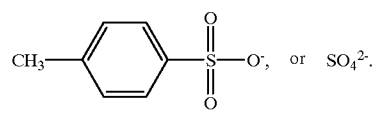

5. Compound according to claim 1 or 2, wherein $R^1$ is $CH_3$, $R^2$ to $R_5$ are each H and $A^{n-}$ is

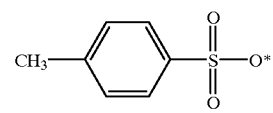

6. A compound according to claim 3, wherein $A^{n-}$ is selected from Cl⁻, Br⁻, I⁻,

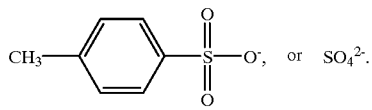

7. A compound according to claim 3, wherein $R^1$ is $CH_3$, $R^2$ to $R^5$ are each H and $A^{n-}$ is

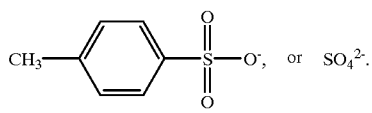

8. A compound according to claim 4, wherein $R^1$ is $CH_3$, $R^2$ to $R^5$ are each H and $A^{n-}$ is

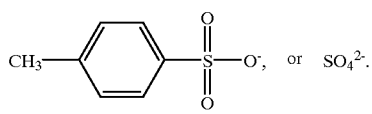

9. A method of treating a patient in need of a photosensitizer comprising administering an effective amount of a compound according to claim 1 and irradiating said patient by light.

10. A method of preparing a compound of claim 1 comprising reacting a compound of the formula

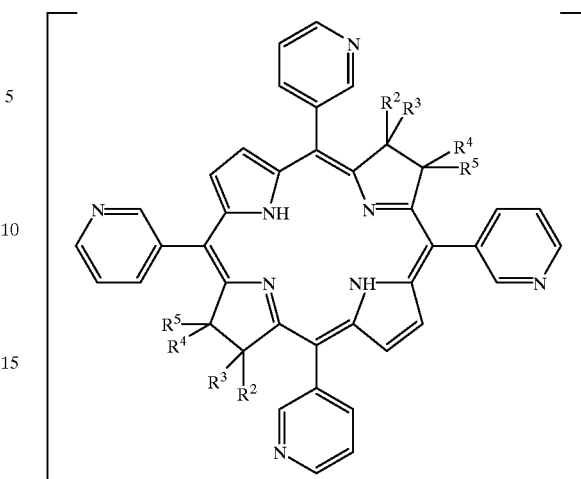

in which $R^2$ to $R^5$ are each H, with a compound of the formula $R^1A^{n-}$, wherein $R^1$ is $C_1$ to $C_6$ alkyl or aryl, and $A^{n-}$ is an anion selected from the group consisting of Cl⁻, Br⁻, I⁻,

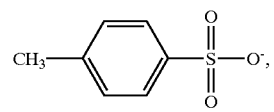

and $SO_4^{2-}$.

* * * * *